United States Patent
Hamersky et al.

(10) Patent No.: US 12,403,083 B2
(45) Date of Patent: Sep. 2, 2025

(54) DISSOLVABLE SOLID STRUCTURE COMPRISING FIRST AND SECOND POLYMERIC STRUCTURANTS

(71) Applicant: The Procter & Gamble Company, Cincinnati, OH (US)

(72) Inventors: Mark William Hamersky, Hamilton, OH (US); Jennifer Elaine Hilvert, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/898,685

(22) Filed: Aug. 30, 2022

(65) Prior Publication Data

US 2023/0060806 A1    Mar. 2, 2023

Related U.S. Application Data

(60) Provisional application No. 63/238,220, filed on Aug. 30, 2021.

(51) Int. Cl.
*A61K 8/81* (2006.01)
*A61K 8/02* (2006.01)
*A61Q 5/12* (2006.01)

(52) U.S. Cl.
CPC .......... *A61K 8/8176* (2013.01); *A61K 8/0216* (2013.01); *A61Q 5/12* (2013.01); *A61K 2800/594* (2013.01)

(58) Field of Classification Search
CPC ............... A61K 8/8176; A61K 8/0216; A61K 2800/594; A61K 8/342; A61K 8/416; A61K 8/42; A61Q 5/12
USPC .................................................. 424/70, 701
See application file for complete search history.

(56) References Cited

U.S. PATENT DOCUMENTS

| | | |
|---|---|---|
| 1,421,350 A | 6/1922 | Powell |
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,648,635 A | 8/1953 | Jacques et al. |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,157,611 A | 11/1964 | Lindemann |
| 3,236,733 A | 2/1966 | Karsten et al. |
| 3,293,718 A | 12/1966 | Melvin |
| 3,321,425 A | 5/1967 | Karl-ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,452,382 A | 7/1969 | Kazdan |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,859,125 A | 1/1975 | Miller |
| 3,875,300 A | 4/1975 | Homm et al. |
| 3,904,543 A | 9/1975 | Knighten |
| 3,929,678 A | 12/1975 | Laughlin |
| 3,943,949 A | 3/1976 | Ashton et al. |
| 3,954,113 A | 5/1976 | Bohrer et al. |
| 3,957,921 A | 5/1976 | Iwahashi et al. |
| 3,967,921 A | 7/1976 | Haberli et al. |
| 4,020,156 A | 4/1977 | Murray et al. |
| 4,024,078 A | 5/1977 | Gilbert et al. |
| 4,033,365 A | 7/1977 | Klepak et al. |

(Continued)

FOREIGN PATENT DOCUMENTS

| | | |
|---|---|---|
| AU | 2004202461 B2 | 11/2007 |
| CA | 2300638 A1 | 8/2000 |

(Continued)

OTHER PUBLICATIONS

"Green Chemistry", Huazhong University of Science and Technology Press, published on Jun. 30, 2008, pp. 6.
Afifi-Effat et al., Polymer Letters, 9: 651-655 (1971).
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009, year 2009, 1 pg.
Ashland, KLUCEL hydroxypropylcelllose, accessed at http://www.ashland.com/Ashland/Static/Documents/ASI/PC_11229_Klucel_HPC.pdf on Apr. 20, 2016.

(Continued)

*Primary Examiner* — Frederick F Krass
*Assistant Examiner* — Lucy M Tien
(74) *Attorney, Agent, or Firm* — Alexandra S. Anoff

(57) ABSTRACT

A dissolvable solid structure that is formed by a homogeneous mixture. The mixture includes from about 1% to about 10% of a first polymeric structurant having a molecular weight of from about 1,000,000 g/mol to about 4,000,000 g/mol, from about 10% to about 20% of a second polymeric structurant having a molecular weight of from about 50,000 g/mol to about 500,000 g/mol, from about 10 wt % to about 85 wt % of one or more high melting point fatty material having a carbon chain length C12-C22 or mixtures thereof and a melting point above 25° C., and from about 1 wt % to about 60 wt % of a cationic surfactant. The dissolvable solid structures can provide an adequate strength during manufacturing, while not deteriorating usage feel when used and/or applied by consumers.

14 Claims, No Drawings

(56) References Cited

U.S. PATENT DOCUMENTS

| | | |
|---|---|---|
| 4,051,081 A | 9/1977 | Jabs et al. |
| 4,089,945 A | 5/1978 | Brinkman et al. |
| 4,149,551 A | 4/1979 | Benjamin et al. |
| 4,180,558 A | 12/1979 | Franklin |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,286,016 A | 8/1981 | Dimond |
| 4,287,219 A | 9/1981 | Fabre |
| 4,315,965 A | 2/1982 | Mason |
| 4,323,525 A | 4/1982 | Bornat |
| 4,323,683 A | 4/1982 | Bolich, Jr. et al. |
| 4,340,583 A | 7/1982 | Wason |
| 4,342,813 A | 8/1982 | Erickson |
| 4,345,080 A | 8/1982 | Bolich, Jr. |
| 4,349,531 A | 9/1982 | Mlodozeniec |
| D266,829 S | 11/1982 | Yoshizawa et al. |
| 4,377,615 A | 3/1983 | Suzuki |
| 4,379,753 A | 4/1983 | Bolich, Jr. |
| 4,381,919 A | 5/1983 | Jacquet et al. |
| 4,415,617 A | 11/1983 | D Elia |
| 4,422,853 A | 12/1983 | Jacquet et al. |
| 4,448,699 A | 5/1984 | Barrat et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |
| D286,450 S | 10/1986 | Tovey |
| 4,635,351 A | 1/1987 | Koch et al. |
| 4,637,859 A | 1/1987 | Trokhan |
| 4,639,390 A | 1/1987 | Shoji |
| 4,663,158 A | 5/1987 | Wolfram et al. |
| 4,683,001 A | 7/1987 | Floyd |
| 4,710,374 A | 12/1987 | Grollier et al. |
| 4,723,362 A | 2/1988 | Boerger |
| 4,727,410 A | 2/1988 | Higgins, III |
| 4,822,613 A | 4/1989 | Rodero |
| 4,885,107 A | 12/1989 | Wetzel |
| 4,892,758 A | 1/1990 | Serbiak |
| 4,923,660 A | 5/1990 | Willenberg |
| 4,976,953 A | 12/1990 | Orr et al. |
| 4,990,280 A | 2/1991 | Thorengaard |
| 5,034,421 A | 7/1991 | Fuisz |
| 5,041,252 A | 8/1991 | Fujii |
| 5,052,296 A | 10/1991 | Shiba |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,110,678 A | 5/1992 | Narukawa |
| 5,112,515 A | 5/1992 | Buxton et al. |
| 5,120,888 A | 6/1992 | Nohr |
| 5,135,804 A | 8/1992 | Harpell |
| 5,158,810 A | 10/1992 | Oishi |
| 5,166,276 A | 11/1992 | Hayama et al. |
| D334,420 S | 3/1993 | Copeland et al. |
| 5,208,104 A | 5/1993 | Ueda |
| 5,220,033 A | 6/1993 | Kamei et al. |
| 5,230,853 A | 7/1993 | Colegrove |
| 5,261,426 A | 11/1993 | Kellett et al. |
| 5,280,079 A | 1/1994 | Allen et al. |
| RE34,584 E | 4/1994 | Grote et al. |
| 5,342,335 A | 8/1994 | Rhim |
| D351,345 S | 10/1994 | Geho |
| 5,362,532 A | 11/1994 | Famili |
| 5,364,627 A | 11/1994 | Song |
| 5,387,147 A | 2/1995 | Ohshima |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee et al. |
| 5,429,628 A | 7/1995 | Trinh et al. |
| 5,429,874 A | 7/1995 | Vanputte |
| 5,446,079 A | 8/1995 | Buchanan et al. |
| 5,455,114 A | 10/1995 | Ohmory |
| 5,457,895 A | 10/1995 | Thompson et al. |
| 5,458,433 A | 10/1995 | Stastny |
| 5,470,424 A | 11/1995 | Isaac |
| 5,470,492 A | 11/1995 | Childs et al. |
| 5,470,653 A | 11/1995 | Honeycutt |
| 5,476,597 A | 12/1995 | Sakata et al. |
| 5,486,418 A | 1/1996 | Ohmory |
| 5,501,238 A | 3/1996 | Borstel et al. |
| 5,518,730 A | 5/1996 | Fuisz |
| 5,520,924 A | 5/1996 | Chapman |
| 5,533,636 A | 7/1996 | Reiker |
| 5,538,735 A | 7/1996 | Ahn |
| 5,580,481 A | 12/1996 | Sakata et al. |
| 5,582,786 A | 12/1996 | Brunskill et al. |
| 5,585,059 A | 12/1996 | Kobayashi |
| D378,180 S | 2/1997 | Hayes et al. |
| 5,651,987 A | 7/1997 | Fuisz |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,691,015 A | 11/1997 | Tsukamoto |
| 5,705,183 A | 1/1998 | Phillips |
| 5,716,692 A | 2/1998 | Warner |
| 5,717,026 A | 2/1998 | Ikimine |
| 5,735,812 A | 4/1998 | Hardy |
| 5,750,122 A | 5/1998 | Evans |
| 5,756,438 A | 5/1998 | Rau et al. |
| 5,780,047 A | 7/1998 | Kamiya et al. |
| 5,780,418 A | 7/1998 | Niinaka |
| D398,847 S | 9/1998 | Wyslotsky et al. |
| D399,260 S | 10/1998 | Thimote |
| 5,827,586 A | 10/1998 | Yamashita |
| 5,840,423 A | 11/1998 | Sano |
| 5,840,675 A | 11/1998 | Yeazell |
| 5,849,378 A | 12/1998 | Gask |
| 5,863,887 A | 1/1999 | Gillette |
| 5,879,493 A | 3/1999 | Johnson |
| D407,640 S | 4/1999 | Crapser et al. |
| D408,223 S | 4/1999 | Henry |
| 5,911,224 A | 6/1999 | Berger |
| 5,914,124 A | 6/1999 | Mahoney |
| 5,925,603 A | 7/1999 | D Angelo |
| 5,942,179 A | 8/1999 | Tallentire |
| 5,952,286 A | 9/1999 | Puvvada et al. |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes et al. |
| D418,750 S | 1/2000 | Blin |
| 6,010,719 A | 1/2000 | Remon et al. |
| 6,028,016 A | 2/2000 | Yahiaoui et al. |
| 6,029,808 A | 2/2000 | Peck et al. |
| 6,034,043 A | 3/2000 | Fujiwara et al. |
| 6,037,319 A | 3/2000 | Dickler |
| 6,066,396 A | 5/2000 | Inada |
| 6,074,997 A | 6/2000 | Rau et al. |
| 6,080,346 A | 6/2000 | Jack |
| D427,902 S | 7/2000 | Hayes et al. |
| 6,106,849 A | 8/2000 | Malkan et al. |
| 6,130,193 A | 10/2000 | Gillette |
| 6,175,054 B1 | 1/2001 | Jacques |
| 6,177,391 B1 | 1/2001 | Zafar |
| 6,197,238 B1 | 3/2001 | Wang |
| 6,200,949 B1 | 3/2001 | Reijmer et al. |
| 6,207,274 B1 | 3/2001 | Ferenc |
| D441,869 S | 5/2001 | Bloor et al. |
| D442,353 S | 5/2001 | Macias |

(56) References Cited

U.S. PATENT DOCUMENTS

| | | |
|---|---|---|
| D442,739 S | 5/2001 | Friesenhahn |
| D443,389 S | 6/2001 | Friesenhahn |
| 6,274,162 B1 | 8/2001 | Steffenino |
| D448,802 S | 10/2001 | Lariviere, Jr. et al. |
| D449,881 S | 10/2001 | Mock, Sr. |
| D450,378 S | 11/2001 | Minakuchi et al. |
| 6,319,510 B1 | 11/2001 | Yates |
| 6,335,312 B1 | 1/2002 | Coffindaffer et al. |
| 6,365,142 B1 | 4/2002 | Tamura |
| 6,382,526 B1 | 5/2002 | Reneker et al. |
| 6,406,797 B1 | 6/2002 | Vanputte |
| 6,417,156 B1 | 7/2002 | Smith et al. |
| 6,420,625 B1 | 7/2002 | Jones |
| 6,426,091 B1 | 7/2002 | Okumura et al. |
| 6,440,926 B1 | 8/2002 | Spadoni et al. |
| D462,900 S | 9/2002 | Yamada et al. |
| 6,448,462 B2 | 9/2002 | Groitzsch |
| 6,458,754 B1 | 10/2002 | Velazquez et al. |
| 6,465,407 B2 | 10/2002 | Hayashi |
| D465,303 S | 11/2002 | Friesenhahn |
| 6,503,521 B1 | 1/2003 | Atis et al. |
| 6,525,034 B2 | 2/2003 | Dalrymple et al. |
| 6,552,123 B1 | 4/2003 | Katayama |
| 6,576,575 B2 | 6/2003 | Griesbach, III |
| 6,608,121 B2 | 8/2003 | Isozaki |
| D479,561 S | 9/2003 | Meyer |
| 6,623,694 B1 | 9/2003 | Ferguson et al. |
| 6,657,004 B2 | 12/2003 | Mizutani |
| D484,749 S | 1/2004 | Garraway |
| 6,699,826 B1 | 3/2004 | Saijo |
| 6,723,160 B2 | 4/2004 | Mackey et al. |
| D489,162 S | 5/2004 | Dings-plooij |
| 6,730,648 B2 | 5/2004 | Gorlin |
| 6,783,852 B2 | 8/2004 | Inada |
| 6,787,512 B1 | 9/2004 | Verrall |
| 6,790,814 B1 | 9/2004 | Marin |
| 6,800,295 B2 | 10/2004 | Fox |
| 6,802,295 B2 | 10/2004 | Bedwell et al. |
| 6,808,375 B2 | 10/2004 | Kloetzer |
| 6,808,598 B1 | 10/2004 | Takeuchi |
| 6,818,606 B1 | 11/2004 | Hanada |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| 6,898,819 B2 | 5/2005 | Tanaka et al. |
| 6,898,921 B2 | 5/2005 | Duffield |
| D509,935 S | 9/2005 | Burt |
| 6,943,200 B1 | 9/2005 | Corrand et al. |
| 6,946,506 B2 | 9/2005 | Bond |
| 6,949,498 B2 | 9/2005 | Murphy |
| 6,956,070 B2 | 10/2005 | Fujiwara |
| 6,977,116 B2 | 12/2005 | Cabell |
| D515,915 S | 2/2006 | Karim |
| 7,015,181 B2 | 3/2006 | Lambino |
| 7,026,049 B2 | 4/2006 | Endo |
| 7,041,369 B1 | 5/2006 | Mackey et al. |
| 7,067,575 B2 | 6/2006 | Kitamura |
| 7,083,047 B2 | 8/2006 | Bone |
| 7,094,744 B1 | 8/2006 | Kobayashi |
| 7,115,551 B2 | 10/2006 | Hasenoehrl |
| 7,125,828 B2 | 10/2006 | Catlin |
| 7,169,740 B2 | 1/2007 | Sommerville-roberts |
| 7,172,765 B2 | 2/2007 | Chu et al. |
| 7,196,026 B2 | 3/2007 | Di Luccio |
| RE39,557 E | 4/2007 | Moe |
| 7,208,460 B2 | 4/2007 | Shefer et al. |
| 7,221,900 B2 | 5/2007 | Reade et al. |
| 7,226,899 B2 | 6/2007 | Cole |
| D549,051 S | 8/2007 | Nordwall |
| 7,285,520 B2 | 10/2007 | Krzysik |
| 7,291,300 B2 | 11/2007 | Chhabra et al. |
| 7,387,787 B2 | 6/2008 | Fox |
| 7,407,669 B2 | 8/2008 | Leung |
| D576,753 S | 9/2008 | Mukai |
| D577,332 S | 9/2008 | Moore |
| 7,429,273 B2 | 9/2008 | De Dominicis |
| D578,881 S | 10/2008 | Friedland et al. |
| 7,446,084 B2 | 11/2008 | Barthel |
| 7,491,407 B2 | 2/2009 | Pourdeyhimi |
| D588,332 S | 3/2009 | Phelan |
| 7,507,698 B2 | 3/2009 | Franzolin |
| 7,547,737 B2 | 6/2009 | Kochvar |
| 7,563,757 B2 | 7/2009 | Kouvroukoglou |
| 7,704,328 B2 | 4/2010 | Bailey et al. |
| 7,708,840 B2 | 5/2010 | Wiedemann |
| 7,727,946 B2 | 6/2010 | Catalfamo |
| 7,824,588 B2 | 11/2010 | Yang |
| 7,832,552 B2 | 11/2010 | Newman |
| 7,846,462 B2 | 12/2010 | Spadini et al. |
| 7,856,989 B2 | 12/2010 | Karles |
| 7,892,992 B2 | 2/2011 | Kamada et al. |
| 7,901,696 B2 | 3/2011 | Eknoian et al. |
| 7,967,801 B2 | 6/2011 | Hammons |
| D640,921 S | 7/2011 | Caldwell |
| D644,541 S | 9/2011 | Schrader et al. |
| 8,049,061 B2 | 11/2011 | Ehrenreich et al. |
| D651,096 S | 12/2011 | Nakagiri |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,232 B2 | 1/2013 | Pourdeyhimi |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,453,653 B2 | 6/2013 | Mishra et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. et al. |
| 8,785,361 B2 | 7/2014 | Sivik et al. |
| D712,159 S | 9/2014 | Clerici et al. |
| D712,822 S | 9/2014 | Brusaw et al. |
| 8,962,501 B2 | 2/2015 | Johnson et al. |
| 8,980,816 B2 | 3/2015 | Dreher |
| 9,005,635 B2 | 4/2015 | Darcy et al. |
| 9,062,186 B2 | 6/2015 | Longdon et al. |
| 9,074,305 B2 | 7/2015 | Glenn, Jr. et al. |
| D739,227 S | 9/2015 | Mitchell et al. |
| 9,125,811 B2 | 9/2015 | Tojo et al. |
| 9,139,802 B2 | 9/2015 | Weisman et al. |
| D740,928 S | 10/2015 | Bruining et al. |
| 9,163,205 B2 | 10/2015 | Sivik et al. |
| 9,173,826 B2 | 11/2015 | Schwartz et al. |
| 9,175,250 B2 | 11/2015 | Sivik et al. |
| 9,198,838 B2 | 12/2015 | Glenn, Jr. et al. |
| D748,240 S | 1/2016 | Goode |
| 9,421,153 B2 | 8/2016 | Sivik et al. |
| D769,522 S | 10/2016 | Venet |
| D771,788 S | 11/2016 | Duckwitz |
| 9,480,628 B2 | 11/2016 | Sivik et al. |
| D774,086 S | 12/2016 | Montes et al. |
| D775,198 S | 12/2016 | Montes et al. |
| 9,539,444 B2 | 1/2017 | Kinoshita et al. |
| 9,545,364 B2 | 1/2017 | Glenn, Jr. et al. |
| D778,026 S | 2/2017 | Roetheli |
| D793,025 S | 8/2017 | Slusarczyk et al. |
| D797,551 S | 9/2017 | Chatterton et al. |
| D798,143 S | 9/2017 | Chatterton |
| D808,583 S | 1/2018 | Zietek |
| 9,902,077 B2 | 2/2018 | Park et al. |

(56) References Cited

U.S. PATENT DOCUMENTS

| | | |
|---|---|---|
| D811,922 S | 3/2018 | Lefave |
| D811,935 S | 3/2018 | Hughes |
| D819,836 S | 6/2018 | Noël |
| 10,045,915 B2 | 8/2018 | Glenn, Jr. et al. |
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,646,413 B2 | 5/2020 | Sivik et al. |
| 10,694,917 B2 | 6/2020 | Dreher et al. |
| D901,115 S | 11/2020 | Carlson et al. |
| D903,152 S | 11/2020 | Chao |
| 10,821,056 B2 | 11/2020 | Swartz et al. |
| D906,802 S | 1/2021 | Chi |
| 10,894,005 B2 | 1/2021 | Sivik et al. |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 11,351,094 B2 | 6/2022 | Hamersky et al. |
| 11,395,789 B2 | 7/2022 | Pratt et al. |
| 11,419,808 B2 | 8/2022 | Hilvert et al. |
| 11,679,066 B2 | 6/2023 | Song et al. |
| 12,018,232 B2 | 6/2024 | Macnamara |
| 2001/0037851 A1 | 11/2001 | Mortellite |
| 2002/0018906 A1 | 2/2002 | Clark |
| 2002/0044968 A1 | 4/2002 | Van Lengerich |
| 2002/0064510 A1 | 5/2002 | Dalrymple et al. |
| 2002/0077264 A1 | 6/2002 | Roberts et al. |
| 2002/0081732 A1 | 6/2002 | Bowlin et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0161088 A1 | 10/2002 | Kochvar |
| 2002/0169092 A1 | 11/2002 | Alexandre et al. |
| 2002/0173213 A1 | 11/2002 | Chu |
| 2002/0175449 A1 | 11/2002 | Chu et al. |
| 2002/0176827 A1 | 11/2002 | Rajaiah |
| 2002/0177621 A1 | 11/2002 | Hanada et al. |
| 2002/0187181 A1 | 12/2002 | Godbey et al. |
| 2003/0013369 A1 | 1/2003 | Soane et al. |
| 2003/0017208 A1 | 1/2003 | Ignatious |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0045446 A1 | 3/2003 | Dihora |
| 2003/0054966 A1 | 3/2003 | Bone et al. |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0114332 A1 | 6/2003 | Ramcharan et al. |
| 2003/0141662 A1 | 7/2003 | Kost et al. |
| 2003/0166489 A1 | 9/2003 | Van Asten et al. |
| 2003/0166495 A1 | 9/2003 | Wang |
| 2003/0180242 A1 | 9/2003 | Eccard et al. |
| 2003/0185872 A1 | 10/2003 | Kochinke |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0216098 A1 | 11/2003 | Carlyle |
| 2003/0224959 A1 | 12/2003 | Smith |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott et al. |
| 2004/0053808 A1 | 3/2004 | Raehse et al. |
| 2004/0059055 A1 | 3/2004 | Inada et al. |
| 2004/0071742 A1 | 4/2004 | Popplewell |
| 2004/0071755 A1 | 4/2004 | Fox |
| 2004/0082239 A1 | 4/2004 | Di Luccio et al. |
| 2004/0092635 A1 | 5/2004 | Kitamura |
| 2004/0108615 A1 | 6/2004 | Foley |
| 2004/0110656 A1 | 6/2004 | Casey et al. |
| 2004/0116018 A1 | 6/2004 | Fenwick et al. |
| 2004/0116539 A1 | 6/2004 | Biercevicz et al. |
| 2004/0118852 A1 | 6/2004 | Barmore et al. |
| 2004/0126585 A1 | 7/2004 | Kerins et al. |
| 2004/0167256 A1 | 8/2004 | Verrall |
| 2004/0170836 A1 | 9/2004 | Bond |
| 2004/0175404 A1 | 9/2004 | Shefer |
| 2004/0180597 A1 | 9/2004 | Kamada |
| 2004/0202632 A1 | 10/2004 | Gott et al. |
| 2004/0204543 A1 | 10/2004 | Yang |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2004/0253434 A1 | 12/2004 | Patel |
| 2004/0254086 A1 | 12/2004 | Hedges et al. |
| 2004/0266300 A1 | 12/2004 | Isele et al. |
| 2005/0003048 A1 | 1/2005 | Pearce |
| 2005/0003991 A1 | 1/2005 | Macquarrie |
| 2005/0008776 A1 | 1/2005 | Chhabra |
| 2005/0010010 A1 | 1/2005 | Kitamura |
| 2005/0069575 A1 | 3/2005 | Fox |
| 2005/0118237 A1 | 6/2005 | Krzysik et al. |
| 2005/0136112 A1 | 6/2005 | Gonzales |
| 2005/0136772 A1 | 6/2005 | Chen et al. |
| 2005/0136780 A1 | 6/2005 | Clark et al. |
| 2005/0137115 A1 | 6/2005 | Cole et al. |
| 2005/0137272 A1 | 6/2005 | Gaserod |
| 2005/0159730 A1 | 7/2005 | Kathrani et al. |
| 2005/0180962 A1 | 8/2005 | Raz et al. |
| 2005/0186256 A1 | 8/2005 | Dihel |
| 2005/0202992 A1 | 9/2005 | Grandio et al. |
| 2005/0209574 A1 | 9/2005 | Boehringer |
| 2005/0220745 A1 | 10/2005 | Lu |
| 2005/0232954 A1 | 10/2005 | Yoshinari et al. |
| 2005/0253297 A1 | 11/2005 | Pedmo et al. |
| 2005/0267005 A1 | 12/2005 | Dasque et al. |
| 2005/0272836 A1 | 12/2005 | Yaginuma et al. |
| 2005/0281757 A1 | 12/2005 | Ibrahim |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0035042 A1 | 2/2006 | Morken |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0083784 A1 | 4/2006 | Ignatious |
| 2006/0089276 A1 | 4/2006 | Klotz |
| 2006/0127458 A1 | 6/2006 | Kiser |
| 2006/0128592 A1 | 6/2006 | Ross et al. |
| 2006/0134412 A1 | 6/2006 | Mackey |
| 2006/0135026 A1 | 6/2006 | Arendt et al. |
| 2006/0159730 A1 | 7/2006 | Simon |
| 2006/0160453 A1 | 7/2006 | Suh |
| 2006/0189772 A1 | 8/2006 | Scheibel |
| 2006/0228319 A1 | 10/2006 | Vona et al. |
| 2006/0254013 A1 | 11/2006 | Konishi |
| 2006/0254014 A1 | 11/2006 | Konishi |
| 2006/0258251 A1 | 11/2006 | Konishi |
| 2006/0264130 A1 | 11/2006 | Karles |
| 2006/0274263 A1 | 12/2006 | Yacktman et al. |

(56) References Cited

U.S. PATENT DOCUMENTS

| | | |
|---|---|---|
| 2007/0028939 A1 | 2/2007 | Mareri et al. |
| 2007/0054579 A1 | 3/2007 | Baker, Jr. |
| 2007/0098749 A1 | 5/2007 | Eknoian et al. |
| 2007/0099813 A1 | 5/2007 | Luizzi et al. |
| 2007/0110792 A9 | 5/2007 | Simon |
| 2007/0128256 A1 | 6/2007 | Aubrun-sonneville |
| 2007/0134304 A1 | 6/2007 | Aubrun-sonneville |
| 2007/0134481 A1 | 6/2007 | Aubrun-sonneville |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2007/0253926 A1 | 11/2007 | Tadrowski |
| 2007/0259170 A1 | 11/2007 | Brown |
| 2007/0259996 A1 | 11/2007 | Vicari |
| 2007/0269651 A1 | 11/2007 | Denome et al. |
| 2007/0298064 A1 | 12/2007 | Koslow |
| 2008/0008906 A1 | 1/2008 | Catalfamo |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0087293 A1 | 4/2008 | Glenn et al. |
| 2008/0090939 A1 | 4/2008 | Netravali et al. |
| 2008/0095828 A1 | 4/2008 | Privitera et al. |
| 2008/0108748 A1 | 5/2008 | Buckley |
| 2008/0118727 A1 | 5/2008 | Andersen |
| 2008/0131695 A1 | 6/2008 | Aouad et al. |
| 2008/0138492 A1 | 6/2008 | Cingotti |
| 2008/0146481 A1 | 6/2008 | Brown |
| 2008/0149119 A1 | 6/2008 | Shen |
| 2008/0152894 A1 | 6/2008 | Beihoffer et al. |
| 2008/0153730 A1 | 6/2008 | Tsaur et al. |
| 2008/0215023 A1 | 9/2008 | Scavone et al. |
| 2008/0220054 A1 | 9/2008 | Shastri |
| 2008/0226919 A1 | 9/2008 | Hosoda |
| 2008/0242572 A1 | 10/2008 | Icht |
| 2008/0269095 A1 | 10/2008 | Aubrun-sonneville |
| 2008/0276178 A1 | 11/2008 | Fadell et al. |
| 2008/0279905 A1 | 11/2008 | Kawamoto et al. |
| 2008/0292669 A1 | 11/2008 | Deng et al. |
| 2008/0293839 A1 | 11/2008 | Stobby |
| 2009/0004254 A1 | 1/2009 | Maibach |
| 2009/0041820 A1 | 2/2009 | Wu et al. |
| 2009/0054860 A1 | 2/2009 | Young et al. |
| 2009/0061225 A1 | 3/2009 | Bailey et al. |
| 2009/0061496 A1 | 3/2009 | Kuhn |
| 2009/0061719 A1 | 3/2009 | Shibutani |
| 2009/0144913 A1 | 6/2009 | Yu et al. |
| 2009/0155326 A1 | 6/2009 | Mack |
| 2009/0155383 A1 | 6/2009 | Kitko et al. |
| 2009/0181587 A1 | 7/2009 | Kang |
| 2009/0197787 A1 | 8/2009 | Venet et al. |
| 2009/0232873 A1 | 9/2009 | Glenn, Jr. et al. |
| 2009/0247036 A1 | 10/2009 | Shi et al. |
| 2009/0249558 A1 | 10/2009 | Fileccia |
| 2009/0258099 A1 | 10/2009 | Brown et al. |
| 2009/0263342 A1 | 10/2009 | Glenn, Jr. et al. |
| 2009/0285718 A1 | 11/2009 | Privitera |
| 2009/0286437 A1 | 11/2009 | Cunningham et al. |
| 2009/0291282 A1 | 11/2009 | Kitamura et al. |
| 2009/0293281 A1 | 12/2009 | Bruno |
| 2009/0312220 A1 | 12/2009 | Boutoille |
| 2010/0018641 A1 | 1/2010 | Branham |
| 2010/0021517 A1 | 1/2010 | Ahlers |
| 2010/0098745 A1 | 4/2010 | Staab |
| 2010/0105821 A1 | 4/2010 | Verrall |
| 2010/0135921 A1 | 6/2010 | Hughes et al. |
| 2010/0150976 A1 | 6/2010 | Schnitzler et al. |
| 2010/0166854 A1 | 7/2010 | Michniak-kohn |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0196440 A1 | 8/2010 | Stark |
| 2010/0266668 A1 | 10/2010 | Coffee |
| 2010/0279905 A1 | 11/2010 | Glenn, Jr. |
| 2010/0285101 A1 | 11/2010 | Moore |
| 2010/0286011 A1 | 11/2010 | Glenn, Jr. et al. |
| 2010/0291165 A1 | 11/2010 | Glenn, Jr. et al. |
| 2010/0298188 A1 | 11/2010 | Glenn, Jr. et al. |
| 2011/0014252 A1 | 1/2011 | Sagel et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0045041 A1 | 2/2011 | Golubovic-liakopoulos et al. |
| 2011/0123596 A1 | 5/2011 | Baecker et al. |
| 2011/0129510 A1 | 6/2011 | Liebmann |
| 2011/0136719 A1 | 6/2011 | Jalbert |
| 2011/0159267 A1 | 6/2011 | Lee |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. et al. |
| 2011/0195098 A1 | 8/2011 | Glenn, Jr. et al. |
| 2011/0223381 A1 | 9/2011 | Sauter |
| 2011/0230112 A1 | 9/2011 | Rose |
| 2011/0250256 A1 | 10/2011 | Hyun-oh et al. |
| 2011/0287687 A1 | 11/2011 | Kramer et al. |
| 2011/0301070 A1 | 12/2011 | Ochomogo |
| 2012/0021026 A1 | 1/2012 | Glenn, Jr. |
| 2012/0027838 A1 | 2/2012 | Gordon et al. |
| 2012/0048769 A1 | 3/2012 | Sivik |
| 2012/0052036 A1 | 3/2012 | Glenn, Jr. |
| 2012/0052037 A1 | 3/2012 | Sivik et al. |
| 2012/0053103 A1 | 3/2012 | Sivik |
| 2012/0053108 A1 | 3/2012 | Glenn, Jr. |
| 2012/0058100 A1 | 3/2012 | Shastri et al. |
| 2012/0058166 A1 | 3/2012 | Glenn, Jr. |
| 2012/0082037 A1 | 4/2012 | Wang |
| 2012/0107534 A1 | 5/2012 | Wnuk et al. |
| 2012/0172831 A1 | 7/2012 | Darcy |
| 2012/0215148 A1 | 8/2012 | Ewert |
| 2012/0237576 A1 | 9/2012 | Gordon |
| 2012/0258902 A1 | 10/2012 | Parrish et al. |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0052277 A1 | 2/2013 | Weiss et al. |
| 2013/0142852 A1 | 6/2013 | Tojo et al. |
| 2013/0171421 A1 | 7/2013 | Weisman |
| 2013/0230482 A1 | 9/2013 | Saguchi et al. |
| 2013/0236520 A1 | 9/2013 | Popovsky et al. |
| 2013/0280979 A1 | 10/2013 | Mckee |
| 2013/0303419 A1 | 11/2013 | Glenn, Jr. et al. |
| 2014/0017402 A1 | 1/2014 | Kleinwaechter et al. |
| 2014/0039114 A1 | 2/2014 | Hagihara et al. |
| 2014/0105946 A1 | 4/2014 | Glenn, Jr. et al. |
| 2014/0127145 A1 | 5/2014 | Deckner |
| 2014/0128345 A1 | 5/2014 | Woodrow et al. |
| 2014/0265007 A1 | 9/2014 | Bruning et al. |
| 2014/0271744 A1 | 9/2014 | Glenn, Jr. et al. |
| 2014/0271745 A1 | 9/2014 | Glenn, Jr. et al. |
| 2014/0287973 A1 | 9/2014 | Sivik |
| 2014/0329428 A1 | 11/2014 | Glenn, Jr. et al. |
| 2015/0044157 A1 | 2/2015 | Kulkarni et al. |
| 2015/0071572 A1 | 3/2015 | Dreher |
| 2015/0102307 A1 | 4/2015 | Tajima et al. |
| 2015/0157548 A1 | 6/2015 | De Feij et al. |
| 2015/0297494 A1 | 10/2015 | Mao et al. |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |
| 2016/0008235 A1 | 1/2016 | Sivik et al. |
| 2016/0010041 A1 | 1/2016 | Sivik et al. |
| 2016/0101026 A1 | 4/2016 | Pratt et al. |
| 2016/0101204 A1 | 4/2016 | Lynch et al. |
| 2016/0143827 A1 | 5/2016 | Castan Barberan et al. |
| 2016/0250109 A1 | 9/2016 | Dreher et al. |

(56) References Cited

U.S. PATENT DOCUMENTS

| | | | |
|---|---|---|---|
| 2016/0324741 A1 | 11/2016 | Baig | |
| 2016/0367104 A1 | 12/2016 | Dreher et al. | |
| 2017/0121641 A1 | 5/2017 | Smith | |
| 2017/0319876 A1 | 11/2017 | Hentrich et al. | |
| 2017/0335080 A1 | 11/2017 | Mao et al. | |
| 2018/0015643 A1 | 1/2018 | Patel et al. | |
| 2018/0104177 A1 | 4/2018 | Constantine et al. | |
| 2018/0110710 A1 | 4/2018 | Zhao et al. | |
| 2018/0140469 A1 | 5/2018 | Kane et al. | |
| 2018/0163325 A1* | 6/2018 | Glenn, Jr. | D01D 5/423 |
| 2018/0258555 A1 | 9/2018 | Glenn, Jr. | |
| 2018/0311135 A1 | 11/2018 | Chang et al. | |
| 2018/0333339 A1* | 11/2018 | Hamersky | A61K 8/41 |
| 2018/0334644 A1 | 11/2018 | Hamersky et al. | |
| 2018/0338890 A1 | 11/2018 | Glenn, Jr. | |
| 2019/0015875 A1 | 1/2019 | Gardner, Jr. et al. | |
| 2019/0105243 A1 | 4/2019 | Song et al. | |
| 2019/0282457 A1 | 9/2019 | Pratt et al. | |
| 2019/0282461 A1 | 9/2019 | Glassmeyer et al. | |
| 2019/0350819 A1* | 11/2019 | Hamersky | A61K 8/463 |
| 2020/0071851 A1 | 3/2020 | Glenn, Jr. et al. | |
| 2020/0093710 A1 | 3/2020 | Hamersky et al. | |
| 2020/0214946 A1 | 7/2020 | Chan et al. | |
| 2020/0261326 A1 | 8/2020 | Sivik et al. | |
| 2020/0275818 A1 | 9/2020 | Dreher et al. | |
| 2020/0308360 A1 | 10/2020 | Mao et al. | |
| 2020/0405587 A1 | 12/2020 | Song | |
| 2021/0000733 A1 | 1/2021 | Hilvert | |
| 2021/0094744 A1 | 4/2021 | Benson et al. | |
| 2021/0107263 A1 | 4/2021 | Bartolucci et al. | |
| 2021/0121373 A1 | 4/2021 | Tan et al. | |
| 2021/0128417 A1 | 5/2021 | Sivik et al. | |
| 2021/0137798 A1 | 5/2021 | Sivik et al. | |
| 2021/0147763 A1 | 5/2021 | Tan et al. | |
| 2021/0189602 A1 | 6/2021 | Glenn, Jr. et al. | |
| 2021/0261885 A1 | 8/2021 | Tibbs et al. | |
| 2021/0322290 A1 | 10/2021 | Lynch et al. | |
| 2021/0401677 A1 | 12/2021 | Song | |
| 2022/0054365 A1 | 2/2022 | Xu et al. | |
| 2022/0257476 A1 | 8/2022 | Hamersky et al. | |
| 2022/0323309 A1 | 10/2022 | Pratt et al. | |
| 2023/0190588 A1 | 6/2023 | Song | |

FOREIGN PATENT DOCUMENTS

| | | |
|---|---|---|
| CA | 2524099 A1 | 4/2006 |
| CA | 2695068 A1 | 9/2010 |
| CA | 166297 | 5/2018 |
| CA | 169627 S | 5/2018 |
| CN | 1138091 | 12/1996 |
| CN | 1219388 | 6/1999 |
| CN | 1268558 | 10/2000 |
| CN | 1357613 A | 7/2002 |
| CN | 1454231 A | 11/2003 |
| CN | 1530431 A | 9/2004 |
| CN | 1583991 A | 2/2005 |
| CN | 1726074 A | 1/2006 |
| CN | 3648760 | 5/2007 |
| CN | 101161877 A | 4/2008 |
| CN | 101280467 A | 10/2008 |
| CN | 101424009 A | 5/2009 |
| CN | 101538745 A | 9/2009 |
| CN | 301666535 | 9/2011 |
| CN | 103735428 A | 4/2014 |
| CN | 304115833 | 4/2017 |
| CN | 106726634 A | 5/2017 |
| CN | 106728634 A | 5/2017 |
| CN | 106916659 A | 7/2017 |
| CN | 304537587 | 3/2018 |
| DE | 19607851 A1 | 9/1997 |
| DE | 10331767 A1 | 2/2005 |
| DE | 102007011606 A1 | 9/2008 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1048722 A1 | 11/2000 |
| EP | 1160311 A2 | 12/2001 |
| EP | 1214879 A2 | 6/2002 |
| EP | 1227152 A1 | 7/2002 |
| EP | 1275368 A1 | 1/2003 |
| EP | 1306425 A2 | 5/2003 |
| EP | 1217987 B1 | 12/2004 |
| EP | 1574561 A1 | 9/2005 |
| EP | 1375377 B1 | 10/2005 |
| EP | 1614790 A1 | 1/2006 |
| EP | 1409628 B1 | 2/2006 |
| EP | 1512701 B1 | 6/2006 |
| EP | 1887036 A2 | 2/2008 |
| EP | 1888036 | 2/2008 |
| EP | 1958532 A2 | 8/2008 |
| EP | 2085434 A1 | 8/2009 |
| EP | 1436376 B1 | 4/2010 |
| EP | 2226379 A1 | 9/2010 |
| EP | 1317916 B1 | 10/2010 |
| EP | 2246031 A1 | 11/2010 |
| EP | 1948771 B1 | 12/2010 |
| EP | 2319965 A1 | 5/2011 |
| EP | 2363432 A1 | 9/2011 |
| EP | 2363517 A1 | 9/2011 |
| EP | 2395142 A1 | 12/2011 |
| FR | 2871685 A1 | 12/2005 |
| FR | 2886845 A1 | 12/2006 |
| GB | 2107579 A | 5/1983 |
| GB | 2235204 A | 2/1991 |
| GB | 2355008 A | 4/2001 |
| GB | 2375542 A | 11/2002 |
| GB | 2378407 A | 2/2003 |
| GB | 2449418 A | 11/2008 |
| HU | 221299 B1 | 9/2002 |
| IN | 20150354411 | 5/2017 |
| JP | S4912158 A | 2/1974 |
| JP | 58021608 | 2/1983 |
| JP | S58216109 A | 12/1983 |
| JP | S59163458 A | 9/1984 |
| JP | S6272609 A | 4/1987 |
| JP | S6272610 A | 4/1987 |
| JP | S6281432 A | 4/1987 |
| JP | S6281462 A | 4/1987 |
| JP | 62156348 | 7/1987 |
| JP | S6346251 A | 2/1988 |
| JP | S63156715 A | 6/1988 |
| JP | H01172319 A | 7/1989 |
| JP | H01229805 A | 9/1989 |
| JP | H01313418 A | 12/1989 |
| JP | H0243268 A | 2/1990 |
| JP | H0275650 A | 3/1990 |
| JP | H02280771 A | 11/1990 |
| JP | 3040879 A | 2/1991 |
| JP | 3101618 A | 4/1991 |
| JP | H05344873 A | 12/1993 |
| JP | H0617083 A | 1/1994 |
| JP | H06116568 A | 4/1994 |
| JP | 0753349 | 2/1995 |
| JP | H0789852 A | 4/1995 |
| JP | H07173724 A | 7/1995 |
| JP | H08325133 A | 12/1996 |
| JP | H09216809 A | 8/1997 |
| JP | H09216909 A | 8/1997 |
| JP | 09279457 | 10/1997 |
| JP | 10008364 A | 1/1998 |
| JP | H101824 A | 1/1998 |
| JP | 10158700 A | 6/1998 |
| JP | H10251371 A | 9/1998 |
| JP | H10251952 A | 9/1998 |
| JP | H10512929 A | 12/1998 |
| JP | H11505569 A | 5/1999 |
| JP | H11513053 A | 11/1999 |
| JP | 2000053998 A | 2/2000 |
| JP | 2000169896 A | 6/2000 |
| JP | 2000212828 A | 8/2000 |
| JP | 2000229841 A | 8/2000 |
| JP | 2001302868 A | 10/2001 |
| JP | 2001519376 A | 10/2001 |

(56) References Cited

FOREIGN PATENT DOCUMENTS

| | | |
|---|---|---|
| JP | 2002201531 A | 7/2002 |
| JP | 2002226895 A | 8/2002 |
| JP | 2003073700 A | 3/2003 |
| JP | 2003082397 A | 3/2003 |
| JP | 2003532554 A | 11/2003 |
| JP | 2004256799 A | 9/2004 |
| JP | 2004533551 A | 11/2004 |
| JP | 2004345983 A | 12/2004 |
| JP | 2005509734 A | 4/2005 |
| JP | 2005171063 A | 6/2005 |
| JP | 2005534716 A | 11/2005 |
| JP | 2006002337 A | 1/2006 |
| JP | 2006056835 A | 3/2006 |
| JP | 2006511732 A | 4/2006 |
| JP | 3828217 B2 | 7/2006 |
| JP | 2006249029 A | 9/2006 |
| JP | 2007001889 A | 1/2007 |
| JP | 2007091954 A | 4/2007 |
| JP | 2007197365 A | 8/2007 |
| JP | 2007197540 A | 8/2007 |
| JP | 2007528748 A | 10/2007 |
| JP | 2007533763 A | 11/2007 |
| JP | 4128580 B2 | 5/2008 |
| JP | 2008156807 A | 7/2008 |
| JP | 2008525436 A | 7/2008 |
| JP | 2009079329 A | 4/2009 |
| JP | 2009533569 A | 9/2009 |
| JP | 4510221 B2 | 5/2010 |
| JP | 2010100966 A | 5/2010 |
| JP | 2010126856 A | 6/2010 |
| JP | 2013099467 A | 5/2013 |
| JP | 5344873 B2 | 8/2013 |
| JP | 5821609 B2 | 10/2015 |
| JP | 6272610 B2 | 1/2018 |
| KR | 20020003442 A | 1/2002 |
| KR | 20040094520 A | 11/2004 |
| RU | 19735 U1 | 10/2001 |
| RU | 2192451 C2 | 11/2002 |
| RU | 2300196 C2 | 6/2007 |
| RU | 2347557 C2 | 2/2009 |
| TW | 232027 B | 10/1994 |
| WO | 8301943 A1 | 6/1983 |
| WO | 1992006603 A1 | 4/1992 |
| WO | 1994002377 A1 | 2/1994 |
| WO | 9404650 A2 | 3/1994 |
| WO | 9514495 A1 | 6/1995 |
| WO | 9523888 A1 | 9/1995 |
| WO | 9918182 A1 | 4/1999 |
| WO | 9951715 A1 | 10/1999 |
| WO | 9957155 A1 | 11/1999 |
| WO | 2000013680 A2 | 3/2000 |
| WO | 0042992 A2 | 7/2000 |
| WO | 0107194 A1 | 2/2001 |
| WO | 0110421 A1 | 2/2001 |
| WO | 0119948 A1 | 3/2001 |
| WO | 0125322 A1 | 4/2001 |
| WO | 0125393 A1 | 4/2001 |
| WO | 200125322 A1 | 4/2001 |
| WO | 2001024770 A1 | 4/2001 |
| WO | 200154667 A1 | 8/2001 |
| WO | 2001054667 A1 | 8/2001 |
| WO | 0183657 A2 | 11/2001 |
| WO | 0238722 A2 | 5/2002 |
| WO | 03044153 A1 | 5/2003 |
| WO | 03060007 A1 | 7/2003 |
| WO | 2004009335 A1 | 1/2004 |
| WO | 2004032859 A2 | 4/2004 |
| WO | 2004041991 A1 | 5/2004 |
| WO | 2004081162 A1 | 9/2004 |
| WO | 2005003423 A1 | 1/2005 |
| WO | 2005068604 A1 | 7/2005 |
| WO | 2005070374 A1 | 8/2005 |
| WO | 2005075547 A1 | 8/2005 |
| WO | 2006106514 A2 | 10/2006 |
| WO | 2006130647 A1 | 12/2006 |
| WO | 2007022229 A1 | 2/2007 |
| WO | 2007033598 A1 | 3/2007 |
| WO | 2007089259 A1 | 8/2007 |
| WO | 2007093558 A1 | 8/2007 |
| WO | 2007093619 A1 | 8/2007 |
| WO | 2007102119 A1 | 9/2007 |
| WO | 2008015641 A2 | 2/2008 |
| WO | 2008049242 A1 | 5/2008 |
| WO | 2008104954 A2 | 9/2008 |
| WO | 2008149248 A2 | 12/2008 |
| WO | 2009019571 A2 | 2/2009 |
| WO | 2009022761 A1 | 2/2009 |
| WO | 2007014221 A3 | 4/2009 |
| WO | 2009095891 A1 | 8/2009 |
| WO | 2009103576 A1 | 8/2009 |
| WO | 2009121900 A1 | 10/2009 |
| WO | 2010006708 A1 | 1/2010 |
| WO | 2010015709 A2 | 2/2010 |
| WO | 2010077627 A2 | 7/2010 |
| WO | 2010085569 A1 | 7/2010 |
| WO | 2011153023 A1 | 12/2011 |
| WO | 2012003349 A2 | 1/2012 |
| WO | 2012120199 A1 | 9/2012 |
| WO | 2014158472 A1 | 10/2014 |
| WO | 2015034975 A1 | 3/2015 |
| WO | 2015153185 A1 | 10/2015 |
| WO | 100932 | 4/2018 |
| WO | 100938 | 4/2018 |
| WO | 101063 | 5/2018 |
| WO | 101100 | 5/2018 |
| WO | 101101 | 5/2018 |
| WO | 2018109200 A1 | 6/2018 |
| WO | 2018140675 A1 | 8/2018 |
| WO | 2019001940 A1 | 1/2019 |
| WO | 2020192519 A1 | 10/2020 |

OTHER PUBLICATIONS

Briscoe et al. "The effects of hydrogen bonding upon the viscosity of aqueous poly( vinyl alcohol) solutions," from Polymer, 41 (2000), pp. 3851-3860.

Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2SdAT7LTehpyxM1qTGtnFETDa1Nuo9_cQSOpPwCmsmmdGA1Y0USekQEaAh0iEALw_wcB (Year: 2021).

Dahiya, A., Karnath, M.G., Hegde, R.R. Melt Blown Technology, Updated Apr. 2004, downloaded from the sitehttp://www.engr.utk.edu/mse/Textiles/Melt%20Blown%20Technology.htm on Dec. 12, 2015.

Definition of Derivative by Merriam Webster Online Dictionary, Year, 2021, 1 Page.

Design of "Detergent tablets" (Design Registration No. 000634142-0003), (No. of Publicly known information: HH18274488), Registered Community Designs Bulletin, published by EUIPO on Jan. 9, 2007, 4 pgs.

Design of "Detergent tablets" (Design Registration No. 000634142-0004), (No. of Publicly known information: HH18274489), Registered Community Designs Bulletin, published by EUIPO on Jan. 9, 2007, 4 pgs.

Dow, UCARE™ Polymer LR-400, Technical Data Sheet, Downloaded in Mar. 2022, 4 pages.

Encyclopedia of Polymer Science and Engineering, vol. 15, 2nd ed., pp. 204 308 Silicones, year 1989.

Francis Ignatious, Linghong Sun, Chao-Pin Lee, and John Baldoni. Electrospun Nanofibers in Oral Drug Delivery—ExpertReview. Pharmaceutical Research, vol. 27, No. 4, Apr. 2010, pp. 576-588. Published online Feb. 9, 2010.

Gemz Hair Care. Perfect Pairs. Publication date unavailable. Visited Jan. 26, 2022. https://shopgemz.com/collections/perfect-pairs (Year: 0).

Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.

(56) References Cited

OTHER PUBLICATIONS

Hildebrand, T., et al. "Quantification of bone microarchitecture with the structure mode index", Computer Methods in Biomechanics and Biomedical Engineering, vol. 1, Jan. 14, 1997, pp. 15-23.

Hiroshi Yagi & 4 Others, Research Study of a Friction Protector for Preventing a Tow Line From Breaking, Working Papers for Fiscal 2006 | Japan | Japan Coast Guard IDec. 2007, pp. 1-8.

How Gemz work?, Gemz Hair Care, published on Oct. 1, 2018, retrieved on Apr. 27, 2021, retrieved from the Internet URL: https://www.youtube.com/watch?v=ts1waYk43g4, 3 pgs.

Karen Duis et al., "Environmental fate and effects of water-soluble synthetic organic polymers used in cosmetic products", Environmental Sciences Europe, vol. 33, Article No. 21, Feb. 16, 2021, 78 pages.

Latorre Carmen, Nanotribological Effects of Hair Careproducts and Environment On Human Hair Using Atomic Forcemicroscopy,Journal of Vacuum Science and Technology: Part A, U.S.A, AVS/AIP , Jun. 28, 2005 , V2 3 N 4, p. 1034-1045.

Makadia, et al., "Poly Lactic-co-Glycolic Acid (PLGA) as Biodegradable ControlledDrug Delivery Carrier", Polymers, 3, pp. 1377-1397 (2011).

Menard et al., "Gnotobiotic Mouse Immune Response Induced by *Bifidobacterium* sp. Strains Isolated from Infants", Applied and Environmental Microbiology, vol. 74, Issue 3, Feb. 1, 2008, pp. 660-666.

Michelle Villett, Why You Need a Sulfate-Free Shampoo, The Skincare Edit, updated date: Jan. 25, 2019, Original publication date: Feb. 22, 2016 (Year: 2016), 7 pages. Mar. 23, 2021.

Minifibers, Inc., accessed on line at http://www.minifibers.com/documents/Choosing-the-Proper-Short-Cut-Fiber.pdf Oct. 3, 2016.

Ni Genshan et al. "Drug Classification and Pharmacology Summary", PLA Press, published on Apr. 30, 1988, pp. 3.

Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.

Overview of pharmaceutical excipients used in tablets and capsules in Drug Topics, dated Oct. 24, 2008. Downloaded Sep. 20, 2016 from http://drugtopics.modernmedicine.com/drugtopics/news/modernmedicine/modernmedicinenews/overviewpharmaceuticalexcipientsusedtablets.

Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).

Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/, 14 pgs.

Retrieved from: https ://www.craftcuts.com/hexagon-craft-shape. html Hexagon wood cutouts, www.craftcuts.com, 1 page, reviewed as early as May 2018 (Year: 2018), 16 pgs.

Rounded hexagon shape, announced 2016 [online], [site visited Oct. 20, 2021], Available from internet, URL:https://www.vexels.com/png-svg/preview/139199/rounded-hexagon-shape (Year: 2016).

Sahin et al. "A Study on Physical and Chemical Properties of Cellulose Paper Immersed in Various Solvent Mixtures" International Journal Of Molecular Sciences, Jan. 2008; 9(1): 78-88.

Smith, et al., "Nanofibrous Scaffolds and Their Biological Effects", Nantechnologiesfor the Life Sciences, vol. 9, pp. 188-215 (2006).

Vaughan, C.D. "Solubility, Effects in Product, Package, Penetration and Preservation", Cosmetics and Toiletries, vol. 103, Oct. 1988, 24 pgs.

Vesterby, A.: "Star Volume in Bone Research: A Histomorphometric Analysis Of Trabecular Bone Structure Using Vertical Sections", Anal Rec: Feb. 1993, 232(2), pp. 325-334.

W S Ratnayake and D S Jackson. Gelatinization and solubility of corn starch during heating in excess water. Facultyu Publications in Food Science and Technology, Jan. 1, 2006. Also published in Journal of Agricultural and Food Chemistry 54:1 O(2006), pp. 3712-3716.

Wang, et al., "A Novel Controlled Release Drug Delivery System for Multiple DrugsBased on Electrospun Nanofibers Containing Nanoparticles", Journal ofPharmaceutical Sciences, vol. 99, No. 12 (Dec. 2010).

PCT Search Report and Written Opinion for PCT/US2022/075613 dated Feb. 3, 2023, 12 pages.

Design Gazette (Application No. 3019850005996), "Design of Soaps", Korean Intellectual Property Office (KIPO), published on Jun. 9, 1986, 3 pgs.

Final Office Action; U.S. Appl. No. 13/173,639 dated Oct. 10, 2014.
Final Office Action; U.S. Appl. No. 13/173,639 dated Nov. 14, 2012.
Final Office Action; U.S. Appl. No. 13/173,639 dated Nov. 19, 2015.
Final Office Action; U.S. Appl. No. 13/229,825 dated Feb. 14, 2022.
Final Office Action; U.S. Appl. No. 13/229,825 dated Feb. 19, 2020.
Final Office Action; U.S. Appl. No. 13/229,825 dated Feb. 21, 2023.
Final Office Action; U.S. Appl. No. 13/229,825 dated Mar. 6, 2015.
Final Office Action; U.S. Appl. No. 13/229,825 dated Mar. 7, 2013.
Final Office Action; U.S. Appl. No. 13/229,825 dated Jun. 5, 2019.
Final Office Action; U.S. Appl. No. 13/229,825 dated Oct. 13, 2016.
Final Office Action; U.S. Appl. No. 13/229,825 dated Dec. 11, 2018.
Final Office Action; U.S. Appl. No. 13/229,825 dated Dec. 18, 2020.
Final Office Action; U.S. Appl. No. 14/334,862 dated Sep. 22, 2016.
Final Office Action; U.S. Appl. No. 15/374,486 dated Apr. 19, 2019.
Final Office Action; U.S. Appl. No. 15/979,961 dated Jan. 29, 2020.

L'Alimentation article, Dizolve Group Corporation, Nov. 2010, p. 28.

Non-Final Office Action; U.S. Appl. No. 13/173,639 dated Mar. 12, 2015.
Non-Final Office Action; U.S. Appl. No. 13/173,639 dated May 23, 2012.
Non-Final Office Action; U.S. Appl. No. 13/173,639 dated Oct. 7, 2013.
Non-Final Office Action; U.S. Appl. No. 13/229,825 dated Apr. 28, 2016.
Non-Final Office Action; U.S. Appl. No. 13/229,825 dated Jul. 10, 2018.
Non-Final Office Action; U.S. Appl. No. 13/229,825 dated Aug. 6, 2014.
Non-Final Office Action; U.S. Appl. No. 13/229,825 dated Aug. 28, 2012.
Non-Final Office Action; U.S. Appl. No. 13/229,825 dated Sep. 3, 2020.
Non-Final Office Action; U.S. Appl. No. 13/229,825 dated Sep. 7, 2022.
Non-Final Office Action; U.S. Appl. No. 13/229,825 dated Sep. 17, 2021.
Non-Final Office Action; U.S. Appl. No. 13/229,825 dated Sep. 30, 2019.
Non-Final Office Action; U.S. Appl. No. 14/334,862 dated Sep. 3, 2015.
Non-Final Office Action; U.S. Appl. No. 15/374,486 dated Aug. 8, 2019.
Non-Final Office Action; U.S. Appl. No. 15/374,486 dated Oct. 5, 2018.
Non-Final Office Action; U.S. Appl. No. 15/978,503 dated Apr. 22, 2021.
Non-Final Office Action; U.S. Appl. No. 15/978,503 dated Jun. 15, 2020.
Non-Final Office Action; U.S. Appl. No. 15/978,503 dated Dec. 23, 2020.
Non-Final Office Action; U.S. Appl. No. 15/979,961 dated Jul. 17, 2020.
Non-Final Office Action; U.S. Appl. No. 15/979,961 dated Aug. 2, 2019.
Non-Final Office Action; U.S. Appl. No. 16/674,837 dated Mar. 14, 2023.
Non-Final Office Action; U.S. Appl. No. 16/674,837 dated Mar. 24, 2023.
Non-Final Office Action; U.S. Appl. No. 17/184,712 dated Jun. 15, 2023.

(56) References Cited

OTHER PUBLICATIONS

Non-Final Office Action; U.S. Appl. No. 17/730,390 dated Apr. 27, 2022.
Notice of Allowance; U.S. Appl. No. 15/170,125 dated Oct. 3, 2016.
Notice of Allowance; U.S. Appl. No. 15/978,503 dated Aug. 9, 2021.
Notice of Allowance; U.S. Appl. No. 15/979,961 dated Feb. 4, 2022.
Notice of Allowance; U.S. Appl. No. 15/979,961 dated Apr. 18, 2022.
Notice of Allowance; U.S. Appl. No. 15/979,961 dated May 3, 2021.
Notice of Allowance; U.S. Appl. No. 15/979,961 dated Aug. 19, 2021.
Notice of Allowance; U.S. Appl. No. 15/979,961 dated Sep. 15, 2021.
Notice of Allowance; U.S. Appl. No. 15/979,961 dated Oct. 14, 2021.
Rowe et al., "Polyvinyl Alcohol", Handbook of Pharmaceutical Excipients Sixth Edition, Pharmaceutical Press, published in 2009, 5 pages.
Wermuth, "Similarity in Drugs: Reflections on Analogue Design", Drug Discovery, Drug Discovery Today, vol. 11 No. 7/8, Apr. 2006; pp. 348-354.
Yasuhiro Hiramatsu et al. "Bifidobacterium Components Have Immunomodulatory Characteristics Dependent on the Method of Preparation" Cytotechnology, Kluwer Academic Publishers, Do, vol. 55, Issue No. 2-3, Nov. 1, 2007, p. 79-87.
Pattama Taepaiboon, et al., "Effect of Cross-linking on Properties and ReleaseCharacteristics of Sodium Salicylate-loaded Electrospun Poly (Vinyl Alcohol) FibreMats", Nanotechnology, vol. 18, No. 17, Apr. 2, 2007.
Wikipedia "Polyvinyl alcohol," URL Link—https://en.wikipedia.org/wiki/Polyvinyl_alcohol, dated May 25, 2017, 5 pgs.
"Prill", wikipedia, https://en.wikipedia.org/wiki/Prill, No Known date, 1 Page.
da Rosa Zavareze, E. et al., Impact of heat-moisture treatment and annealing in starches: A review, Carbohydrate polymers, 83(2), 2011, pp. 317-328.
Database GNPD Mintel, "Dishes & Hands Camp Soap Sheets", XP093208089, Database accession No. 1636025, dated Oct. 6, 2011, 02 Pages.
Database GNPD Mintel, "Soap Leaves", XP093208087, Database accession No. 5336785, dated Dec. 21, 2017, 02 Pages.
Non-Final Office Action; U.S. Appl. No. 16/674,837 dated Dec. 4, 2024.
Zhang et al. "Study on Morphology of Electrospun Poly( vinyl alcohol) Mats," European Polymer Journal 41 (2005), pp. 423-432.

\* cited by examiner

DISSOLVABLE SOLID STRUCTURE COMPRISING FIRST AND SECOND POLYMERIC STRUCTURANTS

FIELD OF THE INVENTION

The present invention relates to a dissolvable solid structure, wherein the dissolvable solid structure is formed by a homogeneous mixture comprising, by weight of the structure: from about 1% to about 10% of a first polymeric structurant having a molecular weight of from about 1,000,000 g/mol to about 4,000,000 g/mol; from about 10% to about 20% of a second polymeric structurant having a molecular weight of from about 50,000 g/mol to about 500,000 g/mol; from about 10 wt % to about 85 wt % of one or more high melting point fatty material having a carbon chain length C12-C22 or mixtures thereof, wherein the melting point is above 25° C.; and from about 1 wt % to about 60 wt % of a cationic surfactant. The dissolvable solid structures of present invention provide an adequate strength during manufacturing, while not deteriorating usage feel when used and/or applied by consumers.

BACKGROUND OF THE INVENTION

Many personal care and other consumer products in the market today are sold in liquid form. While widely used, liquid products often have tradeoffs in terms of packaging, storage, transportation, and convenience of use. Liquid consumer products typically are sold in bottles which add cost as well as packaging waste, much of which ends up in land-fills.

Hair Care products in the form of a dissolvable solid structures present an attractive form to consumers. Market executions of dissolvable solid structures may include, dissolvable films, compressed powders in a solid, fibrous structures, porous foams, soluble deformable solids, powders, etc.

For example, US Patent Application Publication No. 2018/0333339 A discloses a dissolvable solid structure which can be in the form of a fibrous structure comprising: (a) a polymeric structurant having a weight average molecular weight of from about 10,000 g/mol to about 6,000,000 g/mol; (b) a high melting point fatty compound such as a fatty amphiphile, and (c) a cationic surfactant.

However, a need still exists for such dissolvable solid structures, especially for those containing a high melting point fatty compound and a cationic surfactant, which have an adequate strength during manufacturing, while not deteriorating usage feel when used and/or applied by consumers.

SUMMARY OF THE INVENTION

The present invention is directed to a dissolvable solid structure, wherein the dissolvable solid structure is formed by a homogeneous mixture comprising, by weight of the structure:

from about 1% to about 10% of a first polymeric structurant having a molecular weight of from about 1,000,000 g/mol to about 4,000,000 g/mol;

from about 10% to about 20% of a second polymeric structurant having a molecular weight of from about 50,000 g/mol to about 500,000 g/mol;

from about 10 wt % to about 85 wt % of one or more high melting point fatty material having a carbon chain length C12-C22 or mixtures thereof, wherein the melting point is above 25° C.; and from about 1 wt % to about 60 wt % of a cationic surfactant.

It has now been surprisingly found by the present inventors that, by the use of the first and second polymeric structurants having specific molecular weights, the dissolvable solid structures of present invention provide an adequate strength during manufacturing, while not deteriorating usage feel when used and/or applied by consumers.

DETAILED DESCRIPTION OF THE INVENTION

Definitions

As used herein, The Dissolvable Solid Structure may be referred to herein as "the Dissolvable Solid Structure", "the Structure", or "the Dissolvable Structure".

As used herein, "dissolvable" means that the Dissolvable Solid Structure is completely soluble in water or it provides a uniform dispersion upon mixing in water according to the hand dissolution test. The Dissolvable Solid Structure has a hand dissolution value of from about 1 to about 30 strokes, alternatively from about 2 to about 25 strokes, alternatively from about 3 to about 20 strokes, and alternatively from about 4 to about 15 strokes, as measured by the Hand Dissolution Method.

As used herein, "flexible" means a Dissolvable Solid Structure meets the distance to maximum force values discussed herein.

"Fibrous structure" as used herein means a structure that comprises one or more fibrous elements and optionally, one or more particles. The fibrous structure as described herein can mean an association of fibrous elements and optionally, particles that together form a structure, such as a unitary structure, capable of performing a function.

The fibrous structure may have a multi-ply fibrous structure which comprises two or more different fibrous structure plies. Each ply may be the same as or different from other ply.

A layer comprising fibrous elements may sometimes be referred to as a ply. A ply may be a fibrous structure which may be homogeneous or layered as described herein.

The single-ply fibrous structure or a multi-ply fibrous structure comprising one or more fibrous structure plies as described herein may exhibit a basis weight of less than 5000 g/m$^2$ as measured according to the Basis Weight Test Method described herein. For example, the single- or multi-ply fibrous structure may exhibit a basis weight of greater than 10 g/m$^2$ to about 5000 g/m$^2$ and/or greater than 10 g/m$^2$ to about 3000 g/m$^2$ and/or greater than 10 g/m$^2$ to about 2000 g/m$^2$ and/or greater than 10 g/m$^2$ to about 1000 g/m$^2$ and/or greater than 20 g/m$^2$ to about 800 g/m$^2$ and/or greater than 30 g/m$^2$ to about 600 g/m$^2$ and/or greater than 50 g/m$^2$ to about 500 g/m$^2$ and/or greater than 300 g/m$^2$ to about 3000 g/m$^2$ and/or greater than 500 g/m$^2$ to about 2000 g/m$^2$ as measured according to the Basis Weight Test Method.

In one example, the fibrous structure can be a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure may be one or more plies within a multi-ply fibrous structure. In one example, a unitary fibrous structure may comprise three or more different fibrous elements. In another example, a unitary fibrous structure may comprise two or more different fibrous elements.

"Article" as used herein refers to a consumer use unit, a consumer unit dose unit, a consumer use saleable unit, a single dose unit, or other use form comprising a unitary fibrous dissolvable solid structure and/or comprising one or more fibrous structures.

"Fibrous element" as used herein means an elongated particulate having a length greatly exceeding its average diameter, i.e., a length to average diameter ratio of at least about 10. A fibrous element may be a filament or a fiber. In one example, the fibrous element is a single fibrous element rather than a yarn comprising a plurality of fibrous elements.

The fibrous elements may be spun from a filament-forming composition also referred to as fibrous element-forming compositions via suitable spinning process operations, such as meltblowing, spunbonding, electro-spinning, and/or rotary spinning.

The fibrous elements may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongated particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.). Filaments are typically considered continuous or substantially continuous in nature. Filaments are relatively longer than fibers. Non-limiting examples of filaments include meltblown and/or spunbond filaments.

"Fiber" as used herein means an elongated particulate as described above that exhibits a length of less than 5.08 cm (2 in.) and/or less than 3.81 cm (1.5 in.) and/or less than 2.54 cm (1 in.). Fibers are typically considered discontinuous in nature. Non-limiting examples of fibers include staple fibers produced by spinning a filament or filament tow and then cutting the filament or filament tow into segments of less than 5.08 cm (2 in.) thus producing fibers. Therefore, references to filaments herein also include fibers made from such filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element of the present invention such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

As used herein, "porous" means that the Dissolvable Solid Structure has spaces, voids or interstices, (generally referred to herein as "pores") provided by the microscopic complex three-dimensional configuration, that provide channels, paths or passages through which a liquid can flow.

As used herein, "porosity" and "percent porosity" are used interchangeably and each refers to a measure of void volume of the Dissolvable Solid Structure and is calculated as

[1−([basis weight of Dissolvable Solid Structure]/
[thickness of Dissolvable Solid Structure×density of the bulk,dried material])]×100% with the units adjusted so they cancel and multiplied by 100% to provide percent porosity.

The Dissolvable Solid Structure may be referred to herein as "the Dissolvable Solid Structure" or "the Dissolvable Structure".

The term "molecular weight" or "Molecular weight" refers to the weight average molecular weight unless otherwise stated. Molecular weight is measured using industry standard method, gel permeation chromatography ("GPC").

As used herein, the articles including "a" and "an" when used in a claim, are understood to mean one or more of what is claimed or described.

As used herein, the terms "include," "includes," and "including," are meant to be non-limiting.

The methods disclosed in the Test Methods Section of the present application should be used to determine the respective values of the parameters of Applicants' inventions, including those discussed in the Dissolvable Structures—Physical Characteristics section below.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Dissolvable Solid Structure (Dissolvable Solid Articles)

The dissolvable solid structure of the present invention is formed by a homogeneous mixture, comprises, by weight of the structure:
  from about 1% to about 10% of a first polymeric structurant having a molecular weight of from about 1,000,000 g/mol to about 4,000,000 g/mol;
  from about 10% to about 20% of a second polymeric structurant having a molecular weight of from about 50,000 g/mol to about 500,000 g/mol;
  from about 10 wt % to about 85 wt % of one or more high melting point fatty material having a carbon chain length C12-C22 or mixtures thereof, wherein the melting point is above 25° C.; and
  from about 1 wt % to about 60 wt % of a cationic surfactant.

The dissolvable solid structure can be a fibrous structure formed by a plurality of fibrous elements wherein the fibrous elements are formed by the above homogeneous mixture.

The dissolvable solid structure of the present invention can be a personal care product, fore example a hair care product, alternatively rinse-off hair care product, even alternatively rinse-off hair care product containing non-sulfate surfactant.

The dissolvable solid structure may contain particulates. The dissolvable solid structure may have an aesthetic feature selected from the group consisting of printing, embossing, texture, colored and mixtures thereof.

First and Second Polymeric Structurants

The structure comprises:
from about 1% to about 10% of a first polymeric structurant having a molecular weight of from about 1,000,000 g/mol to about 4,000,000 g/mol, alternatively from about 1,500,000 g/mol to about 3,500,000 g/mol; and
from about 10% to about 20% of a second polymeric structurant having a molecular weight of from about 50,000 g/mol to about 500,000 g/mol, alternatively from about 65,000 g/mol to about 395,000 g/mol.

In the present invention, it is preferred the weight ratio between the first and second polyvinylpyrrolidones is from about structurants is from about 1:1 to about 1:100, alternatively from about 1:1 to about 1:50, alternatively from about 1:1 to about 1:10.

In the present invention, it is preferred that the weight ratio between the first and second polymeric structurant is in a range such that the combined average molecular weight of the first and second polymeric structurants is from about 300,000 g/mol to about 3,000,000 g/mol, alternatively from about 350,000 g/mol to about 2,000,000 g/mol, alternatively from about 400,000 g/mol to about 1,000,000 g/mol, and alternatively from about 500,000 g/mol to about 1,000,000 g/mol.

In the present invention, it is preferred that the amounts of the first and second polymeric structurants, the molecular weights of the first and second polymeric structurants, and the weight ratio between the first and second polymeric structurants are selected such that the mixture in melt at 85° C. has a viscosity of from about 0.3 Pa·s to about 10 Pa·s, alternatively from about 3 Pa·s to about 8 Pa·s.

The first and second polymeric structurants are water-soluble polymers. As used in the present invention, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have a solubility in water, measured at 25° C., of from about 0.1 gram/liter (g/L). to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp. The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

Non-limiting examples of such water-soluble polymers can include polyacrylic acid and its copolymers, polyvinylpyrrolidone and its copolymers, polyacrylamide and its copolymers, polyvinylmethyl ether, polyethyleneimine, polymethacrylic acid, other water soluble acrylic polymers such as polyN-isopropyl acrylamide, polyN-N-dimethyl-acrylamide, poly (2-ethyl-2-oxazoline), polyoxazoline, polyvinyloxazolidone, polyvinyl caprolactam, polystyrene sulfonate, polyvinyl formamide, polyvinyl amine, alkylated polyvinyl pyrrolidone, poly vinyl caprolactam, polyvinyl valerolactam, polyvinyl imidazole, polyacrylic acid, polyacrylamide, polymethacrylamide, polydimethacrylamide, polyalkylaminomethacrylate, and polyalkylaminomethacrylamide, and combinations thereof. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl imidazole, acrylic acid, methacrylate, acrylamide, vinyl oxazoline, 2-ethyl-2oxazoline, methacrylamide, dimethacrylamide, alkylaminomethacrylate, and alkylaminomethacrylamide monomers.

Among a variety of the water soluble polymers, the first and second polymeric structurants can be selected from the group consisting of: polyvinylpyrrolidone and its copolymers, and mixtures thereof. alternatively, the first and second polymeric structurants are polyvinylpyrrolidone.

As used herein, "vinyl pyrrolidone copolymer" (and "copolymer" when used in reference thereto) refers to a polymer of the following structure (I):

(I)

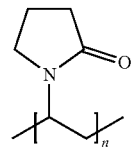

In structure (I), n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, vinyl valerolactam, vinyl oxazoline, 2-ethyl-2oxazoline, vinyl imidazole, acrylic acid, methacrylate, acrylamide, methacrylamide, dimethacrylamide, alkylaminomethacrylate, and alkylaminomethacrylamide monomers.

For example, suitable polymers for use are PVP K120 from Ashland having a weight average molecular weight of about 3,470,000 g/mol, PVP K90 from Ashland having a weight average molecular weight of 1,570,000 g/mol, PVP K60 from Jarchem having a weight average molecular weight of 396,000 g/mol, PVP K30 from Ashland having a weight average molecular weight of 66,800 g/mol. Additional suitable polymers include copolymers of polyvinylpyrrolidone, such as Ganex® or PVP/VA (weight average molecular weight of about 50,000 g/mol) copolymers from Ashland Inc., also performed as suitable structurants but a higher level was utilized to be effective due to their lower weight average molecular weight.

Additional Polymeric Structurant

The structure may further contain an additional structurant. Such additional structurant can be the polymers listed above, but those having different MW from FIRST and SECOND Polymer Structurants.

Cationic Surfactant

The structure further comprises a cationic surfactant at a level of from about 1 wt % to about 60 wt %, alternatively from about 10 wt % to about 50 wt %, alternatively from about 20 wt % to about 40 wt % by weight of the structure.

Cationic surfactant useful herein can be one cationic surfactant or a mixture of two or more cationic surfactants. The cationic surfactant can be selected from the group consisting of, but not limited to: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt, a tertiary amine and combinations thereof.

Mono-Long Alkyl Amine

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines. Primary, secondary, and tertiary fatty amines are useful.

Suitable for use in the dissolvable solid structure are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively l-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

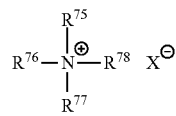

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (I):

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, $C_1$-$C_4$ alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The structure further comprises a high melting point fatty compound at a level of from about 10 wt % to about 85 wt %, alternatively from 20 wt % to 70 wt %, alternatively from about 50 wt % to about 70 wt %, alternatively from about 10 wt % to about 20 wt % by weight of the structure. The fatty compound can be selected from the group consisting of, but not limited to, fatty amphiphiles, fatty alcohol, fatty acid, fatty amide, fatty ester and combinations thereof.

The high melting point fatty compound useful herein have a melting point of 25° C. or higher, alternatively 40° C. or higher, alternatively 45° C. or higher, alternatively 50° C. or higher, in view of stability of the emulsion especially the gel matrix. Such melting point is up to about 90° C., alternatively up to about 80° C., alternatively up to about 70° C., alternatively up to about 65° C., in view of easier manufacturing and easier emulsification. The high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, fatty amides, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols can be used in the composition described herein. The fatty alcohols useful herein are those having from about 14 to about 30 carbon atoms, alternatively from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

Generally, in the mixture, the weight ratio of cetyl alcohol to stearyl alcohol is from about 1:9 to 9:1, alternatively from about 1:4 to about 4:1, alternatively from about 1:2.3 to about 1.5:1.

When using higher level of total cationic surfactant and high melting point fatty compounds, the mixture has the weight ratio of cetyl alcohol to stearyl alcohol of from about 1:1 to about 4:1, alternatively from about 1:1 to about 2:1, alternatively from about 1.2:1 to about 2:1, in view of maintaining acceptable consumer usage. It may also provide more conditioning on damaged part of the hair.

Dispersing Agent

The structure may further comprise a dispersing agent for increasing the wetting, hydration, and/or dispersion of the conditioner materials. The dispersing agent can be included at a level of from about 1 wt % to about 30 wt %, alternatively from about 5 wt % to about 15 wt %, and alternatively from about 5 wt % to about 10 wt % by weight of the second layer. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, gluconamides, cocoamiodpropyl betaines, alkyl glucoside, triethanol amine, cocamide MEAs and mixtures thereof.

Plasticizer

The structure may optionally comprise from about 1 wt % to about 25 wt % plasticizer, in one embodiment from about 3 wt % to about 20 wt % plasticizer, in one embodiment from about 5 wt % to about 15 wt % plasticizer. by weight of the layer.

When present in the Structures, non-limiting examples of suitable plasticizing agents include polyols, copolyols, polycarboxylic acids, polyesters and dimethicone copolyols.

Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol, isosorbide, glucamine, N-methylglucamine and other mono- and polyhydric low molecular weight alcohols (e.g., $C_2$-$C_8$ alcohols); mono di- and oligo-saccharides such as fructose, glucose, sucrose, maltose, lactose, and high fructose corn syrup solids and ascorbic acid.

Examples of polycarboxylic acids include, but are not limited to citric acid, maleic acid, succinic acid, polyacrylic acid, and polymaleic acid.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate.

Examples of suitable dimethicone copolyols include, but are not limited to, PEG-12 dimethicone, PEG/PPG-18/18 dimethicone, and PPG-12 dimethicone.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyaluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

EP 0283165 B1 discloses suitable plasticizers, including glycerol derivatives such as propoxylated glycerol.

Optional Ingredients

The first and/or the second layer may comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1992.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, antidandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Further non-limiting examples of optional ingredients include encapsulated perfumes, such as by β-cyclodextrins, polymer microcapsules, starch encapsulated accords and combinations thereof.

Suitable conditioning agents include high melting point fatty compounds, silicone conditioning agents and cationic conditioning polymers. Suitable materials are discussed in US 2008/0019935, US 2008/0242584 and US 2006/0217288.

Physical Properties of the Dissolvable Solid Structure

For fibrous Structures, the Structure comprises a significant number of dissolvable fibers with an average diameter less than about 150 micron, alternatively less than about 100 micron, alternatively less than about 10 micron, and alternatively less than about 1 micron with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, alternatively at least 25% of all the dissolvable fibers, alternatively at least 50% of all the dissolvable fibers, alternatively at least 75% of all the dissolvable fibers. The significant number may be at least 99% of all the dissolvable fibers. Alternatively, from about 50% to about 100% of all the dissolvable fibers may have an average diameter less than about 10 micron. The dissolvable fibers produced by the method of the present disclosure have a significant number of dissolvable fibers with an average diameter less than about 1 micron, or sub-micron fibers. In an embodiment, Dissolvable Solid Structure may have from about 25% to about 100% of all the dissolvable fibers with an average diameter less than about 1 micron, alternatively from about 35% to about 100% of all the dissolvable fibers with an average diameter less than about 1 micron, alternatively from about 50% to about 100% of all the dissolvable fibers with an average diameter less than about 1 micron, and alternatively from about 75% to about 100% of all the dissolvable fibers with an average diameter less than about 1 micron.

The percent porosity of the dissolvable solid Structure is at least about 25%, alternatively at embodiment at least about 50%, alternatively at least about 60%, alternatively at least about 70% and alternatively at least about 80%. The porosity of the dissolvable solid Structure is not more than about 99%, alternatively not more than about 98%, alternatively not more than about 95%, and alternatively not more than about 90%. Porosity of a Structure is determined according to the procedure set forth in the definition of "porosity" above.

A range of effective sizes of pores can be accommodated. The pore size distribution through the Structure cross-section may be symmetric or asymmetric.

The Structure can be flexible and have a distance to maximum force value of from about 6 mm to about 30 mm. The distance to maximum force value from about 7 mm to about 25 mm, alternatively from about 8 mm to about 20 mm, and alternatively from about 9 mm to about 15 mm.

The Structure can be characterized in one aspect by its Specific Surface Area. The Structure can have a Specific Surface Area of from about 0.03 $m^2$/g to about 0.25 $m^2$/g, alternatively from about 0.035 $m^2$/g to about 0.22 $m^2$/g, alternatively from about 0.04 $m^2$/g to about 0.19 $m^2$/g, and alternatively from about 0.045 $m^2$/g to about 0.16 $m^2$/g.

The Structure can be a flat, flexible Structure in the form of a pad, a strip, or tape and having a thickness of from about 0.5 mm to about 10 mm, alternatively from about 1 mm to about 9 mm, alternatively from about 2 mm to about 8 mm, and alternatively from about 3 mm to about 7 mm as measured by the below methodology. The Structure can be a sheet having a thickness from about 5 mm to about 6.5 mm. Alternatively, two or more sheets are combined to form a Structure with a thickness of about 5 mm to about 10 mm.

The Structure can have a basis weight of from about 200 grams/$m^2$ to about 2,000 grams/$m^2$, alternatively from about 400 g/$m^2$ to about 1,200 g/$m^2$, alternatively from about 600 g/$m^2$ to about 2,000 g/$m^2$, and alternatively from about 700 g/$m^2$ to about 1,500 g/$m^2$.

The Structure can have a dry density of from about 0.08 g/$cm^3$ to about 0.40 g/$cm^3$, alternatively from about 0.08 g/$cm^3$ to about 0.38 g/$cm^3$, alternatively from about 0.10 g/$cm^3$ to about 0.25 g/$cm^3$, and alternatively from about 0.12 g/$cm^3$ to about 0.20 g/$cm^3$.

Method of Use

The dissolvable solid substrates described herein may be used for cleaning and/or treating hair, hair follicles, skin, teeth, and the oral cavity. The method for treating these consumer substrates may comprise the steps of: a) applying an effective amount of the Structure to the hand, b) wetting the Structure with water to dissolve the solid, c) applying the dissolved material to the target consumer substrate such as to clean or treat it, and d) rinsing the diluted treatment composition from the consumer substrate. These steps can be repeated as many times as desired to achieve the desired cleansing and or treatment benefit.

A method useful for providing a benefit to hair, hair follicles, skin, teeth, and/or the oral cavity, includes the step of applying a composition according to the first embodiment to these target consumer substrates in need of regulating.

Alternatively, a useful method for regulating the condition of hair, hair follicles, skin, teeth, the oral cavity, includes the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, alternatively from about 1.0 grams to about 5 grams, and alternatively from about 1.5 grams to about 3 grams.

Product Types and Articles of Commerce

Non-limiting examples of products that utilize the dissolvable solid structures include hand cleansing substrates, teeth cleaning or treating substrates, oral cavity substrates, hair shampoo or other hair treatment substrates, body cleansing substrates, shaving preparation substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and so forth.

The dissolvable solid structure can be a personal care product, alternatively hair care product, alternatively rinse-off hair care product, alternatively rinse-off hair care product containing non-sulfate surfactant.

Described herein is an article of commerce comprising one or more dissolvable solid structures described herein, and a communication directing a consumer to dissolve the Structure and apply the dissolved mixture to hair, hair follicles, skin, teeth, the oral cavity, to achieve a benefit to the target consumer substrate, a rapidly lathering foam, a rapidly rinsing foam, a clean rinsing foam, and combinations thereof. The communication may be printed material attached directly or indirectly to packaging that contains the dissolvable solid structure or on the dissolvable solid structure itself. Alternatively, the communication may be an electronic or a broadcast message that is associated with the article of manufacture. Alternatively, the communication may describe at least one possible use, capability, distinguishing feature and/or property of the article of manufacture.

Test Methods

Basis Weight Measurement

In general, basis weight of a material or article (including the dissolvable solid structure) is measured by first cutting the sample to a known area, using a die cutter or equivalent, then measuring & recording the weight of the sample on a top-loading balance with a minimum resolution of 0.01 g, then finally by calculating the basis weight as follows:

Basis Weight (g/m²)=weight of basis weight pad (g)

$$\text{Basis Weight}\left(\frac{g}{m^2}\right) = \frac{\text{Weight of pad }(g) \times 10{,}000\frac{cm^2}{m^2}}{\text{area of pad }(cm^2)}$$

Suitable pad sample sizes for basis weight determination are >10 cm² and should be cut with a precision die cutter having the desired geometry. If the dissolvable solid structure to be measured is smaller than 10 cm², a smaller sampling area can be sued for basis weight determination with the appropriate changes to calculation.

In the present examples, basis weight was calculated based on the full dissolvable solid structure having a known area of 17.28 cm². Thus, the basis weight calculation becomes:

$$\text{Basis Weight}\left(\frac{g}{m^2}\right) = \frac{\text{Weight of pad }(g) \times 10{,}000\frac{cm^2}{m^2}}{17.28 cm^2}$$

Hand Dissolution Test Method

Materials Needed:

Dissolvable solid structures to be tested: 3-5 dissolvable solid structure s (finished product samples) are tested so that an average of the number of strokes for each if the individual dissolvable solid structure samples is calculated and recorded as the Average Hand Dissolution value for the dissolvable solid structure. For this method, the entire consumer saleable or consumer use dissolvable solid structure is tested. If the entire consumer saleable or consumer use dissolvable solid structure has a footprint greater than 50 cm², then first cut the dissolvable solid structure to have a footprint of 50 cm².

Nitrile Gloves 10 cc syringe

Plastic Weigh boat (~3 in×3 in)

100 mL Glass beaker

Water (City of Cincinnati Water or equivalent having the following properties: Total Hardness=155 mg/L as CaCO2; Calcium content=33.2 mg/L; Magnesium content=17.5 mg/L; Phosphate content=0.0462 mg/L)

Water used is 7 gpg hardness and 40° C.+/−5° C.

Protocol:

1. Add 80 mL of water to glass beaker. Add 300-500 ml of water to glass beaker.
2. Heat water in beaker until water is at a temperature of 40° C.+/−5° C.
3. Transfer 10 mL of the water from the beaker into the weigh boat via the syringe.
4. Within 10 seconds of transferring the water to the weigh boat, place dissolvable solid structure sample in palm of gloved hand (hand in cupped position in non-dominant hand to hold dissolvable solid structure sample).
5. Using dominant hand, add water quickly from the weigh boat to the dissolvable solid structure sample and allow to immediately wet for a period of 5-10 seconds.
6. Rub with opposite dominant hand (also gloved) in 2 rapid circular strokes.
7. Visually examine the dissolvable solid structure sample in hand after the 2 strokes. If dissolvable solid structure sample is completely dissolved, record number of strokes=2 Dissolution Strokes. If not completely dissolved, rub remaining dissolvable solid structure sample for 2 more circular strokes (4 total) and observe degree of dissolution. If the dissolvable solid structure sample contains no solid pieces after the 2 additional strokes, record number of strokes=4 Dissolution Strokes. If after the 4 strokes total, the dissolvable solid structure sample still contains solid pieces of un-dissolved dissolvable solid structure sample, continue rubbing remaining dissolvable solid structure sample in additional 2 circular strokes and check if there are any remaining solid pieces of dissolvable solid structure sample after each additional 2 strokes until dissolvable solid structure sample is completely dissolved or until reaching a total of 30 strokes, whichever comes first. Record the total number of strokes. Record 30 Dissolution Strokes even if solid dissolvable solid structure sample pieces remain after the maximum of 30 strokes.
8. Repeat this process for each of the additional 4 dissolvable solid structure samples.
9. Calculate the arithmetic mean of the recorded values of Dissolution Strokes for the 5 individual dissolvable solid structure samples and record as the Average Hand Dissolution Value for the dissolvable solid structure. The Average Hand Dissolution Value is reported to the nearest single Dissolution Stroke unit.

Fibrous Structures—Fiber Diameter

For fibrous Structures, the diameter of dissolvable fibers in a sample of a web is determined by using a Scanning Electron Microscope (SEM) or an Optical Microscope and image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in microns (µm). Several fibers are thus randomly selected across the sample of the web using the SEM or the optical microscope. At least two specimens from the web (or web inside a product) are cut and tested in this manner. Altogether at least 100 such measurements are made and then all data are recorded for statistical analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micron diameter or %-submicron, for example. We denote the measured diameter (in microns) of an individual circular fiber as di.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $d_{num}$ $$\frac{\sum_{i=1}^{n} d_i}{n}$$

Combinations
1. A dissolvable solid structure, wherein the dissolvable solid structure is formed by a homogeneous mixture comprising, by weight of the structure:
   from about 1% to about 10% of a first polymeric structurant having a molecular weight of from about 1,000,000 g/mol to about 4,000,000 g/mol;
   from about 10% to about 20% of a second polymeric structurant having a molecular weight of from about 50,000 g/mol to about 500,000 g/mol;
   from about 10 wt % to about 85 wt % of one or more high melting point fatty material having a carbon chain length C12-C22 or mixtures thereof, wherein the melting point is above 25° C.; and from about 1 wt % to about 60 wt % of a cationic surfactant.
2. The dissolvable solid structure of the preceding feature, wherein the first and second polymeric structurants are selected from the group consisting of: polyacrylic acid and its copolymers, polyvinylpyrrolidone and its copolymers, polyacrylamide and its copolymers, polyvinylmethyl ether, polyethyleneimine, polymethacrylic acid, poly N-isopropyl acrylamide, poly N—N-dimethylacrylamide, polyvinyloxazolidone, a poly(vinyl oxazoline), poly 2-ethyl-2-oxazoline, polyvinylcaprolactam, polystyrene sulfonate, polyvinyl formamide, polyvinyl amine, poly alkylated vinyl pyrrolidone, poly vinyl valerolactam, polyvinyl imidazole, polyacrylic acid, polymethacrylate, polyacrylamide, polymethacrylamide, polydimethacrylamide, polyalkylaminomethacrylate, and polyalkylaminomethacrylamide, and copolymer combinations thereof.
3. The dissolvable solid structure of any of the preceding features, wherein the first and second polymeric structurants are selected from the group consisting of: polyvinylpyrrolidone and its copolymer, and mixtures thereof, preferably wherein the first and second polymeric structurants are polyvinylpyrrolidone.
4. The dissolvable solid structure of any of the preceding features, wherein the first polymeric structurant has a molecular weight of from about 1,500,000 g/mol to about 3,500,000 g/mol.
5. The dissolvable solid structure of any of the preceding features, wherein the second polymeric structurant has a molecular weight of from about 65,000 g/mol to about 395,000 g/mol.
6. The dissolvable solid structure of any of the preceding features, wherein the weight ratio between the first and second polymeric structurants is from about 1:1 to about 1:100, preferably from about 1:1 to about 1:50, more preferably from about 1:1 to about 1:10.
7. The dissolvable solid structure of any of the preceding features, wherein the weight ratio between the first and second polymeric structurants is in a range such that the average molecular weight of the first and second polymeric structurants is from about 300,000 g/mol to about 3,000,000 g/mol, preferably from about 350,000 g/mol to about 2,000,000 g/mol, more preferably from about 400,000 g/mol to about 1,000,000 g/mol, and even more preferably from about 500,000 g/mol to about 1,000,000 g/mol.
8. The dissolvable solid structure of any of the preceding features, wherein a total amount of the first and second polymeric structurants is from about 11% to about 25% by weight of the structure, preferably from about 13% to about 20% by weight of the structure.
9. The dissolvable solid structure of any of the preceding features, wherein the dissolvable solid structure is a personal care product, preferably hair care product, more preferably rinse-off hair care product, still more preferably rinse-off hair care product containing non-sulfate surfactant.

10. The dissolvable solid structure of any of the preceding features, comprising from about 10 wt % to about 50 wt % of cationic surfactant by weight of the structure, preferably from about 20 wt % to about 40 wt % of cationic surfactant.

11. The dissolvable solid structure of any of the preceding features, wherein the Dissolvable Solid Structure dissolves in less than 30 strokes of the Hand Dissolution Method, preferably wherein the Dissolvable Solid Structure dissolves in less than 20 strokes of the Hand Dissolution Method, and even more preferably wherein the Dissolvable Solid Structure dissolves in less than 15 strokes of the Hand Dissolution Method.

NON-LIMITING EXAMPLES

The compositions illustrated in the following Examples illustrate specific embodiments of the composition, but are not intended to be limiting thereof. Other modifications can be undertaken by the skilled artisan without departing from the spirit and scope of this invention. These exemplified embodiments of the composition as described herein provide enhanced conditioning benefits to the hair.

All exemplified amounts are listed as weight percents and exclude minor materials such as diluents, preservatives, color solutions, imagery ingredients, botanicals, and so forth, unless otherwise specified. All percentages are based on weight unless otherwise specified.

The dissolvable solid structures of Ex.1 to Ex. 5 are examples of the present invention These examples of the present invention provide an adequate strength during manufacturing, while not deteriorating usage feel when used and/or applied by consumers.

The dissolvable solid structures of CEx.i and CEx.ii are comparative examples of the present invention. In CEx.i, the mechanical strength of the fibrous element-forming composition during manufacturing is sufficient, however, its overall hair feel is inferior than the control conditioner. In CEx.ii, the mechanical strength of the fibrous element-forming composition during manufacturing too low while it exhibits acceptable hair feel.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the

| Dissolvable solid structure-Hair conditioner Examples | | | | | | | |
|---|---|---|---|---|---|---|---|
| Raw Material | Ex 1 | Ex 2 | Ex 3 | Ex 4 | Ex 5 | CEx. i | CEx. ii |
| Behentrimonium Methosulfate | 21 | 21.5 | 21.7 | 21.8 | — | — | 25 |
| Behentrimonium Chloride | — | — | — | — | 14 | 20 | — |
| Stearyl Alcohol | 37 | 38 | 38.2 | 38.4 | 41.3 | 35 | 40 |
| 1-Hexadecanol | 15 | 15.5 | 15.6 | 15.7 | 20.7 | 15 | 20 |
| Lauroyl Methyl Glucamide | 10 | 9.5 | 7.8 | 7.8 | 7 | 10 | 10 |
| Polyvinyl pyrrolidone (PVP K30 from Ashland) having MW of 66,800 | 10 | 9.3 | 13.3 | 10.7 | 10 | 18 | — |
| Polyvinyl pyrrolidone (PVP K60 from Jarchem) having MW of 396,000 | — | — | — | 1.6 | — | — | — |
| Polyvinyl pyrrolidone (PVP K90 from Ashland) having MW of 1,570,000 | 5.5 | 5 | 3.3 | — | 5.5 | 5 | — |
| Polyvinyl pyrrolidone (PVP K120 from Ashland) having MW of 3,470,000 | 1.5 | 1.2 | — | 4 | 1.5 | — | 4 |
| Combined average MW of PVPs | 853,412 | 815,177 | 365,629 | 934,255 | 853,412 | 66,800 | 3,470,000 |
| Strength during manufacturing *1 | Pass | Pass | Pass | Pass | Pass | Pass | Fail |
| Usage feel *2 | Pass | Pass | Pass | Pass | Pass | Fail | Pass |

*1 Mechanical strength during any suitable method to manufacturing the dissolvable solid structure which is a fibrous structure formed by a plurality of fibrous elements. For example, the fibrous elements are formed by meltblowing and/or spunbonding, by using a fibrous element-forming composition comprising the above ingredients in the table. The levels of the ingredients in such fibrous element-forming composition are adjusted such that the ingredients have the levels defined above in the dissolvable solid structure.
*2 Usage feel is assessed as follows: Samples provided to 10 panelists who rate the product based on overall hair feel compared to a control conditioner (CEx.ii). "Pass" means that 6 or more panelists answer that the overall hair feel is parity to or superior than the control conditioner.

same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid structure, wherein the dissolvable solid structure is formed by a homogeneous mixture comprising, by weight of the structure:
    polymeric structurants consisting of:
        from about 1% to about 10% of one or more first polymeric structurants wherein the structurants comprise a molecular weight of from about 1,500,000 g/mol to about 3,500,000 g/mol;
        from about 10% to about 20% of or more second polymeric structurants wherein the structurants comprise a molecular weight of from about 65,000 g/mol to about 396,000 g/mol;
        wherein the ratio of the first polymeric structurants to the second polymeric structurants is less than 1:1;
        wherein the first and second polymeric structurants are polyvinylpyrrolidone, its copolymer, or a mixture thereof;
    from about 10 wt % to about 85 wt % of one or more high melting point fatty material comprising a carbon chain length C12-C22 or mixtures thereof and a melting point above 25° C.; and
    from about 1 wt % to about 60 wt % of a cationic surfactant;
    wherein the combined average molecular weight of the first and second polymeric structurants is from about 350,000 g/mol to about 1,000,000 g/mol;
    wherein the dissolvable structure is a hair conditioner.

2. The dissolvable solid structure of claim 1 wherein the first and second polymeric structurants are polyvinylpyrrolidone.

3. The dissolvable solid structure of claim 1, wherein a total amount of the first and second polymeric structurants is from about 11% to about 25% by weight of the structure.

4. The dissolvable solid structure of claim 3, wherein a total amount of the first and second polymeric structurants is from about 13% to about 20% by weight of the structure.

5. The dissolvable solid structure of claim 1, comprising from about 10 wt % to about 50 wt % of cationic surfactant by weight of the structure.

6. The dissolvable solid structure of claim 5, comprising from about 20 wt % to about 40 wt % of cationic surfactant by weight of the structure.

7. The dissolvable solid structure of claim 1, wherein the dissolvable solid structure dissolves in less than 20 strokes, according to a Hand Dissolution Method described herein.

8. The dissolvable solid structure of claim 7, wherein the dissolvable solid structure dissolves in less than 15 strokes, according to the Hand Dissolution Method described herein.

9. The dissolvable solid structure of claim 1, wherein the cationic surfactant is chosen from behentrimonium methosulfate, behentrimonium chloride, or mixtures thereof.

10. The dissolvable solid structure of claim 1, wherein the fatty material is stearyl alcohol.

11. The dissolvable solid structure of claim 1, wherein the structurants consist of two first polymeric structurants and one second polymeric structurant.

12. The dissolvable solid structure of claim 11, wherein the two first polymeric structurants have a molecular weight of about 1,570,000 and about 3,470,000 and the second polymeric structurant has a molecular weight of about 66,800.

13. The dissolvable solid structure of claim 1, wherein the structurants consist of one first polymeric structurant and two second polymeric structurants.

14. The dissolvable solid structure of claim 13, wherein the first polymeric structurant comprises a molecular weight of about 3,470,000 and the two second polymeric structurant comprises a molecular weight of about 66,800 and about 396,000.

* * * * *